United States Patent [19]

Itoh et al.

[11] Patent Number: 5,194,464
[45] Date of Patent: Mar. 16, 1993

[54] ENTERIC FILM AND PREPARATOIN THEREOF

[75] Inventors: Shunichi Itoh, Suita; Hiroyoshi Koyama, Mishima; Toshio Kashihara, Suita; Shin-ichiro Hirai, Kyoto, all of Japan

[73] Assignee: Takeda Chemical Industries, Ltd., Osaka, Japan

[21] Appl. No.: 497,655

[22] Filed: Mar. 23, 1990

Related U.S. Application Data

[63] Continuation-in-part of Ser. No. 412,439, Sep. 26, 1989, abandoned.

[30] Foreign Application Priority Data

Sep. 27, 1988 [JP] Japan .................. 63-243542

[51] Int. Cl.$^5$ .......................... C08L 1/26; C08L 1/08; B05D 7/00
[52] U.S. Cl. .................................. 524/42; 524/43; 524/77; 106/163.1; 106/170; 106/178; 106/180; 106/188; 106/189; 106/197.2; 106/198; 427/3; 427/214; 427/220; 427/221; 424/463
[58] Field of Search .................. 524/42, 43, 77; 424/463; 106/163.1, 170, 178, 180, 188, 198, 189, 191.2; 427/3, 214, 220, 221

[56] References Cited

U.S. PATENT DOCUMENTS

| | | | |
|---|---|---|---|
| 2,949,402 | 8/1960 | Nejad et al. | 427/3 |
| 3,149,039 | 9/1964 | Jefferies | 106/218 |
| 3,256,111 | 6/1966 | Singiser | 427/3 |
| 3,297,535 | 1/1967 | Butler et al. | 106/218 |
| 3,390,049 | 6/1968 | Rednick et al. | 106/218 |
| 3,539,380 | 11/1970 | Johnson | 427/3 |
| 3,738,952 | 6/1973 | Signorinor | 524/77 |
| 4,287,221 | 9/1981 | Tonedachi et al. | 427/3 |
| 4,385,078 | 5/1983 | Onda et al. | 427/3 |
| 4,670,287 | 6/1987 | Tsuji | 424/463 |
| 4,816,259 | 3/1989 | Matthews et al. | 424/463 |

OTHER PUBLICATIONS

Japanese Pharmacopeia, 11th Rev. Ed. "Hydroxy propylmethylcellulose phthalate 200731," Chemical Abstract 111:120929s Enteric-Coating Soft Gelatin Capsules Containing Hydroxypropyl Methyl Cellulose & Polyethylene Glycol.
Catalog of HP-MCP, Shin-Etsu Chemical Company, Ltd., Tokyo, Japan (1985).

Primary Examiner—John Kight, III
Assistant Examiner—P. Hampton-Hightower
Attorney, Agent, or Firm—Wegner, Cantor, Mueller & Player

[57] ABSTRACT

An enteric film is produced by spraying on a material a mixed solution of (a) hydroxypropylmethylcellulose phthalate exhibiting a viscosity of about 136 to 204 centistokes as 10% methanol/dichloromethane (1:1 by weight) solution at 20° C., (b) polyethylene glycol presenting solid state at ambient temperature and (c) shellac, wherein respective ratios of (b) and (c) to (a) are 0.1 to 20 weight percent and 5 to 40 weight percent; and then drying the solution.

The enteric film excels in film strength and acid resistance, and can be employed in pharmaceutical preparations.

17 Claims, No Drawings

ENTERIC FILM AND PREPARATOIN THEREOF

This application is a continuation-in-part of Ser. No. 412,439, filed Sep. 26, 1989, now abandoned.

This invention relates to enteric films having improved strength, thus being usable in such fields as foods and pharmaceuticals.

Generally, enteric coating of pharmaceutical preparations has been carried out for the purposes of the protection of the active ingredient susceptible of the protection of the gastric juice and the drug-release controlled system (or the drug delivery system). In the enteric-coated pharmaceutical preparations, the intended purpose has been heretofore achieved by covering tablet surfaces with the coating. In recent years, however, reports were published that the enteric-coated granules, when compared with the enteric-coated tablets from a biopharmaceutical point of view, do not produce individual variation in gastric emptying rate and absorption and are almost free from influence by meals, and as an example of such granules, there may be mentioned the aspirin preparation [C. Bogentoft, et al.; Eur. J. Clin. Pharmacol., 14, 351-355 (1978) and A. Anslow et al.; Current Therapeutic Research, 36 (5), 811-818 (1984)].

Nevertheless, the conventional enteric films themselves show deteriorated strength, and when granules being provided with the enteric coating are for example pharmaceutically processed into tablets or capsules, such enteric coating films in many instances are destroyed due to mechanical shock during processing and consequently fail to perform the function of the enteric coating For the prevention of such trouble, plasticizers are required to be added, but addition of plasticizers often results in lowered effect of the enteric coating. For example, it is known that addition of polyethylene glycols to hydroxy-propylmethylcellulose phthalate brings about deterioration in the enteric coating performance (for example, refer to the catalogue of Shin-etsu Chem. Ind., Ltd., the 1985 edition HPMCP). Under these circumstances an enteric film having increased film strength and adequately retaining the enteric coating property has been strongly demanded to be developed.

Taking such situations into consideration, the present inventors conducted intensive investigation into the coating base which is usable in the processing and manufacture of enteric granules and enteric powder having increased film strength and as a result: found that when hydroxypropylmethylcellulose phthalate having specifically defined properties, shellac and polyethylene glycol are combined at a specific ratio to conduct enteric coating, there unexpectedly result enteric pharmaceutical preparations with enhanced film strength and furthermore that in cases where they are processed into other types of pharmaceutical preparations such as tablets and capsules, such preparations can withstand mechanical shock or impact, thereby leading to the completion of this invention.

Thus, this invention relates to the enteric film which is composed of (a) hydroxypropylmethylcellulose phthalate having a viscosity of about 136 to 204 centistokes, (b) polyethylene glycol presenting a solid state at ambient temperature and (c) shellac, with the mixing ratio of (b) and (c) to (a) ranging from 0.1 to 20 weight % and from 5 to 40 weight %, respectively.

Hydroxypropylmethylcelluloss phthalate (hereinafter may be referred to as "HPMCP") as used in this invention shows a methoxyl group content of 18.0 to 22.0%, a hydroxypropoxyl group content of 5.0 to 9.0% and a carboxybenzoyl group content of 27.0 to 35.0%, with its mean degree of polymerization of about 240, and exhibits a viscosity (at 20° C.) of about 136 to 204 centistokes as a 10% solution (methanol/dichloromethane 1:1 by weight) (refer to the Japanese Pharmacopoeia, the 11th revised edition, section concerning hydroxypropylmethylcellulose phthalate 200731). Its specific examples include HP-55S (produced by Shin-Etsu Chemical Co., Ltd., Tokyo, Japan).

Polyethylene glycol ( hereinafter referred to in some instances as "PEG") as used in this invention presents the solid form at ambient temperature (15 to 25° C.) and shows normally a mean molecular weight of 1,200 to 25,000, preferably 2,000 to 10,000, more preferably 7,000 to 9,500. Its specific examples include PEG 1500, PEG 4000, PEG 6000 and PEG 20000.

Shellac as used in this invention is a resinous material produced by purification/bleaching of secretions from *Coccus lactis*.

The process for producing enteric films according to this invention is described in the following. Thus, the enteric film of this invention is obtained by covering a pharmaceutical preparation intended to be provided with enteric property with an enteric coating agent consisting of HPMCP, PEG and shellac being formulated at the previously mentioned ratio.

The pharmaceutical preparation to be covered with the said enteric film is not specifically limited, if it includes powders, fine granules, granules (obtained by, for example, extruding granulation process or rotary granulation process), pills, tablets, capsules and pharmaceutically processed products thereof (for example, the products produced by processing enteric powder, enteric fine granules, enteric granules into tablets or capsules). Furthermore, the active ingredients to be incorporated into these pharmaceutical preparations is not specifically limited, if it can be incorporated into the preparations for the purpose of enteric property, and includes, for example, drug substances for the central nervous system, such as diazepam, idebenone, aspirin, ibuprofen, paracetamol, naproxen, piroxicam, dichlofenac, indomethacin, sulindac, lorazepam, intrazepam, phenytoin, acetaminophen, ethenzamide, and ketoprofen; cardiovascular drugs, such as molsidomine, vinpocetine, propranolol, methyldopa, dipyridamol, furosemide, triameren, nifedipine, atenolol, spironolactone, metoprolol, pindolol, captopril and isosorbide dinitrate; drugs for respiratory organs, such as amlexanox, detromethorphan, theophilline, pseudo-ephedrine, salbutamol and guaiphenecin; drugs for digestive organs, such as drugs of benzimidazole series having anti-ulcer activity being exemplified by 2-[(3-methyl-4-(2,2,2-trifluoroethoxy)2-pyridyl)methylsulfinyl]benzimidazole, (hereinafter referred to sometimes as "Compound A") and 5-methoxy-2-[(4-methoxy-3,5-dimethyl-2-pyridyl)-methylsulfinyl]benzimidazole, cimetidine, ranitidine, pancreatin, bisacodyl and 5-aminosalicylic acid; antibiotics and chemotherapeutic agents, such as cephalexin, cephaclor, cefradine, amoxixillin, pivampicillin, bacampicillin, dicloxacillin, erythromycin, erythromycin stearate, lincomycin, doxycycline and trimethoprim/sulfamethoxazole; drugs for the metabolic system, such as serapeptase, lysozyme chloride, adenosine phosphate, glibenclamide, and potassium chloride; and vitamin drugs, such as vitamin $B_1$, vitamin $B_2$, vitamin $B_6$, vitamin C and fursulthiamin. In preparing the said pharmaceutical preparations, there may be incorporated additives which are generally used in processing into pharmaceutical preparations, and the additives alone may be covered with the enteric film of this invention, without incorporating the active ingredient. As the additive, there may be mentioned, for example, excipients (e.g. lactose, corn starch, sucrose, talc, crystalline cellulose, mannitol, light anhydrous silicic acid, magnesium carbonate, calcium carbonate, L-cysteine, etc.), binders (e.g. pregelatinized starch, methylcellulose, carboxymethylcellulose, hydroxypropylcellulose, hydroxypropylmethylcellulose, polyvinylpyrrolidone, pullulan, dextrin, gum arabic, low substituted hydroxypropylcellulose (hereinafter referred to sometimes as "L-HPC"), etc.), disintegrating agents [e.g. calcium carboxymethylcellulose, starch, crosslinked sodium carboxymethylcellulose (hereinafter referred to sometimes as "Ac-Di-Sol"), crosslinked insoluble polyvinyl pyrrolidone, etc.], surfactants (e.g. Pluronic, Tween, polyethylene glycol, etc.), lubricants (e.g. magnesium stearate, talc, etc.), coloring agents (e.g. titanium oxide, ferric oxide, tar dyes, etc.) and the like. These agents may be used in more than two kinds.

As the solvent which is used to dissolve HPMCP, PEG and shellac in this invention, there may be mentioned, for example, mixtures of acetone and ethanol and mixtures of ethanol and water, and alcohols such as isopropanol and n-propanol may be added, if necessary.

HPMCP is desirably dissolved in acetone, whereupon the mixing ratio of HPMCP against acetone is normally 3 to 15 weight %, preferably 6 to 10 weight %. A mixing ratio of less than 3 %, because of the lowered concentration of HPMCP, requires a prolonged period of time to perform the coating in sufficient amounts enough to secure adequate enteric property and is not preferable. A mixing ratio of not less than 20 % results in increased viscosity of the solution, bringing about troubles during coating PEG and shellac are desirably dissolved in ethanol, and if necessary, warming is effected in order to accelerate dissolution. Referring to the mixing ratios of these substances, PEG is dissolved normally at a ratio of 0 1 to 5 weight %, preferably 0.5 to 1.5 weight %, while shellac is dissolved normally at a ratio of 1 to 10 weight %, preferably 3 to 6 weight %.

The enteric coating solution is preferably produced by mixing an acetone solution of HPMCP with an ethanol solution of PEG and shellac. When the said ethanol solution is mixed with the said acetone solution at a ratio of 10 to 100 weight % against the acetone solution, particularly 10 to 70 weight %, there can be obtained a solution mixture free from insoluble matter. The enteric coating solution thus mixed is sprayed onto the objective preparations to give enteric coated pharmaceutical preparations In reference to the composition of three substances in the enteric film of the resulting enteric coated preparation, PEG is normally contained at a ratio of 0.1 to 20 weight %, preferably 2 to 10 weight %, while shellac usually at a ratio of 5 to 40 weight %, preferably 15 to 35 weight %, as expressed on the basis of HPMCP. The three-component compositions are soluble in a mixture consisting of 75 to 85 weight % of alcohol and 15 to 25 weight % of water, particularly in a mixture consisting of 78 to 82 weight % of alcohol and 18 to 22 weight % of water, and when the content of HPMCP in the said mixture is normally at a ratio of 1 to 10 weight %, with PEG and shellac being contained at the above mentioned ratios, excellent enteric coating solutions can be obtained.

Referring in more detail to the method of covering with the previously mentioned enteric coating solution, the enteric coated tablets are obtained for example by placing plain tablets in a ventilated coating machine followed by spraying with the coating solution, whereby no limitation is posed on the type of pharmaceutical preparations to be used for coating. For this purpose, the temperature of the coating solution during production is not specifically required to be adjusted and may usually be at room temperature (1 to 30° C). Furthermore, in the case of granules, for example, core granules are placed in a fluidized coating machine and sprayed with the coating solution without controlling the temperature of the solution as is the case with the coating of tablets. The enteric coated preparations obtained by this procedure may be further treated by means of a per se known method for the purpose of printing or polishing. Also, the enteric coated granules and powders may be pharmaceutically processed into tablets and capsules (hard or soft capsules). In addition, they may be mixed with other types of pharmaceutical preparations produced by a per se known process, for example granules provided with the coating having a varied pH value of dissolution, to give sustained release or gastrointestinal tract targeting pharmaceutical preparations.

Below described are the examples, reference examples and test examples to illustrate this invention more specifically, but the present invention is not understood to be limited by these examples.

The enteric film according to the present invention excels in film strength and acid resistance, and consequently, pharmaceutical preparations such as granules, powders and tablets can be covered with said enteric films to produce the enteric-coated pharamaceutical preparations with increased film strength.

EXAMPLE 1

Charged in a centrifugal fluidized coating granulator (CF-360, manufactured by Freund Co. of Japan) was 2100 g of Nonpareil (20 to 28 mesh), and under 200 rpm rotor speed, coating was carried out through dusting with dusting powder of the below-described composition as obtained in advance by mixing, at a rate of 20 g/minutes, while spraying with 2000 ml of hydroxypropylcellulose solution (3 %(v/v)) at a rate of 25 ml/minute, followed by vacuum drying at 40° C. for 16 hours and sifting through a round sieve to give spherical granules having core of 12 to 32 mesh.

| [Dusting powder] | |
|---|---|
| Compound A | 400 g |
| Magnesium carbonate | 400 g |
| Sucrose | 400 g |
| Corn starch | 400 g |
| L-HPC | 60 g |

(degree of hydroxypropyl substitution: 10.0 to 13.0 % (W/W); average particle size not more than 30 μm. L-HPC with the same degree of substitution and average particle size as described above was used in the examples to be given in the following).

Out of the resulting spherical granules having core, 3800 g was weighed out for sampling and placed in a fluidized-bed coating machine (manufactured by Okawara Co. of Japan), and spraying was carried out with the enteric coating solution of the following composition at a rate of 50 ml/minute, under the inlet air temperature and product temperature being controlled at 60° C. and 45° C., respectively, to give enteric-coated granules. The resulting granules were found to be almost free from granule breaking and binding together among granules during coating, being covered uniformly with enteric films, and to pass the particle size test (the particle size as granules specified in the Japanese Pharmacopeia, 11th revised edition. The same test procedure was adopted in the examples to be described in the following) as well as the acid-resistance (the first solution) and disintegrating property (the second solution) tests in the disintegration test method specified in the Japanese Pharmacopeia, 11th revised edition (the same test procedures were adopted in the examples to be described below).

| [Enteric coating solution] | |
|---|---|
| HP-55S | 780 g |
| Polyethylene glycol 6000 | 8 g |
| Shellac | 120 g |
| Acetone | 13000 g |
| Ethanol | 2400 g |

240 mg of the enteric-coated granules as obtained by the above procedure was filled into a No. 2 hard gelatin capsule (weight: 65 mg) by use of a capsule filling machine (manufactured by Parke-Davis Co. of USA) to give a capsule. The enteric-coated granules in capsules were raken our to investigate into the acid resistance, with the result that there was no problem in the property.

EXAMPLE 2

Charged in a CF granulator (manufactured by Freund Co.) was 42 g of Nonpareil (24 to 32 mesh), and under 60 rpm rotor speed, granulation was performed while spraying with the in-advance prepared coating solution of the following composition at a rate of 200 ml/minute×2 guns. The granulated material was vacuum-dried at 40° C. for 16 hours and sifted through a sieve to give spherical cored granules of 12 to 32 mesh.

| [Coating solution] | |
|---|---|
| Serrapeptase | 3000 g |
| L-HPC | 1600 g |
| Lactose | 160 g |
| Sugar | 1600 g |
| Talc | 1600 g |
| Ethanol | 11500 g |
| Water | 9700 g |

Out of the resulting spherical granules having core, 48 kg was weighed out and placed in a fluidized-bed coating machine (FLO-60, Freund/Okawara Co.), and spraying was carried out with the enteric coating solution of the following composition at a rate of 170 o/-minute×3 guns under the inlet air temperature and outlet air temperature being controlled at 60° C. and about 40° C., respectively, to produce enteric-coated granules having a core. The resulting granules were found to be free from granule breaking during coating, being covered uniformly with enteric films, and to pass the particle size, acid resistance and disintegration tests specified in the Japanese Pharmacopeia.

| [Enteric coating solution] | |
|---|---|
| HP-55S | 11600 g |
| Shellac | 2800 g |
| Polyethylene glycol 6000 | 660 g |
| Ethanol | 56300 g |
| Acetone | 131500 g |

Mixed for 3 minutes in a tumbling mixer (TM-15, manufactured by Showa Kagaku-Kikai Manufacturing Co.) were 420 g of the enteric-coated granules having core as obtained by the above procedure, 270 g of aluminum hydroxide/sodium hydrogencarbonate coprecipitated product, 580 g of crystalline cellulose, 150 g of crosslinked sodium carboxy-methylcellulose, 20 g of magnesium stearate and 1440 g of other granules with the mixing conditions being 10 rpm for 3 minutes). The resultant mixture was compressed into tablets at a compression pressure of 1 ton/cm$^2$, employing Pure Press Correct 19K (manufactured by Kikusui Seisakusho LTD.) with the use of an oblong type punch, to produce white plain tablets each having a weight of 480 mg and 15 mm of major axis, 6.5 mm of minor axis, 6.4 mm of thickness and 1.2 minutes of disintegration time.

[Granules for tablet compression]

A mixture consisting of 900 g of acetaminophen, 7.5 g of chlorpheniramine maleate, 48 g of noscapine, 75 g of anhydrous caffeine, 24 g of dihydrocodeine phosphate, 60 g of di-methylephedrine hydrochloride 72 g of Ac-Di-Sol and 72 g of corn starch was admixed with crystalline cellulose to make up to 1389.6 g, which was mixed adequately in a vertical granulator (FM-G25 type, manufactured by Fuji Sangyo Co.) (mixing conditions: 400 rpm for 10 minutes) and kneaded with an aqueous solution of 50.4 g of hydroxypropylcellulose. The resultant white kneaded material was dried in a fluidized-bed dryer (FD-3S, manufactured by Fuji Sangyo Co.) at the air blowing temperature of 60° C. and passed through a power mill with 1.5 mm$\phi$ punching screen (P-3 type, manufactured by Showa Kagaku-Kikai Seisakusho Co.) to produce granules for tablet.

EXAMPLE 3

Charged into a multiplex granulator (MP-25 type, manufactured by Fuju Sangyo Co.) were 500 g of serrapeptase, 3000 g of sucrose, 150 g of crystalline cellulose, 1050 g of corn starch, 150 g of Ac-Di-Sol and 150 g of hydroxypropylcellulose, and 1450 g of water was added to carry out granulation (granulation conditions: 400 rpm for 15 minutes) The granulated material was subjected to fluidized drying in a multi-processor (FD-MX-1 type, manufactured by Fuji Sangyo-Aeromatic Co.) at the inlet air temperature of 55° C. and sifted through a sieve, whereby the dried material of 32 to 60 mesh was sampled. 2000 g of the dried material was weighed out and placed in the previously mentioned multi-processor (of an aero-coater type used), and spraying was conducted with the enteric coating solution of the following composition at a rate of 50 g/minute under the inlet-air temperature and product temperature being controlled at about 43° C. and about 20° C., respectively,to give enteric-coated granules The granules were found to be free from granule breaking during coating and to be covered uniformly with enteric films. Also, the enteric-coated granules were sifted through a 24 to 32 mesh screen to investigate into acid resistance, with the result that they passed the test specified in the Japanese Pharmacopeia.

| [Enteric coating solution] | |
|---|---|
| HP-55S | 720 g |
| Shellac | 240 g |
| Polyethylene glycol 6000 | 40 g |
| Ethanol | 3000 g |
| Acetone | 7000 g |

EXAMPLE 4

Charged into a fluidized-bed coating machine, Gratt WSG-15 (manufactured by Gratt Co. of West Germany), was 3300 g of the spherical granules having a core as used in Example 2, and spraying was performed with the following enteric coating solution at a rate of 55 g/minute under the inlet-air temperature and product temperature being controlled at about 55° C. and about 43° C., respectively, to give enteric coated granules. The resultant enteric-coated granules were found to be free from granule breaking and binding together among granules during coating, being covered uniformly with enteric films, and to pass the particle size, acid resistance and disintegration tests specified in the Japanese Pharmacopeia.

| [Enteric coating solution] | |
|---|---|
| HP-55S | 770 g |
| Shellac | 187 g |
| Polyethylene glycol 6000 | 44 g |
| Ethanol | 3750 g |
| Acetone | 8770 g |

EXAMPLE 5

Placed in a fluidized-bed coating machine (FD-3S, manufactured by Fuji Sanqvo Co.) was 550 q of the spherical granules having a core as used in Example 2, and spraying was carried out with the below-described enteric coating solution at a rate of 12 g/minute, while making the granules fluidized at the inlet-air temperature of 60° C., to give enteric-coated granules. The resultant granules were found to be free from granule breaking during coating, being covered uniformly with enteric films. Also, the enteric coated granules were sifted through a 24 to 32 mesh screen to investigate into the acid resistance, with the result that they passed the test specified in the Japanese Pharmacopeia.

| [Enteric coating solution] | |
|---|---|
| HP-55S | 140 g |
| Shellac | 34 g |
| Polyethylene glycol 60000 | 8 g |
| Ethanol | 3350 g |
| Water | 840 g |

REFERENCE EXAMPLE 1

In the procedure of Example 4, HP-55 or HP-50 produced by Shinetsu Chemical Ind. Co. of Japan. HP-55 and HP-50 show a viscosity (as a 10 % methanol/dichloromethane solution) of about 32 to 48 centistokes and about 44 to 66 centistokes, respectively]was used in place of HP-55S to prepare enteric coating solutions, and spraying was carried out with the enteric coating solutions to produce enteric-coated granules (Control sections 1 and 2). The resulting enteric-coated granules were found to be free from granule breaking and binding together among granules during coating, being covered uniformly with enteric films, and to pass the particle-size, acid-resistance and disintegration tests specified in the Japanese Pharmacopeia.

REFERENCE EXAMPLE 2

In the procedure of Example 4, castor oil was used in place of shellac and polyethylene glycol 6000 to prepare the following enteric coating solution, which was sprayed to give enteric-coated granules (Control section 3). The resultant enteric-coated granules were found to be free from granule breaking and binding together among granules during coating, being covered uniformly with enteric films, and to pass the particle-size, acid-resistance and disintegration tests specified in the Japanese Pharmacopeia.

| [Enteric coating solution] | |
|---|---|
| HP-55S | 770 g |
| Castor oil | 90 g |
| Ethanol | 1980 g |
| Acetone | 7880 g |

REFERENCE EXAMPLE 3

In the procedure of Example 5, polyethylene glycol 400 or acetylated xonoglyceride (Mybarset 9-40T), a liquid plasticiser, was used in place of polyethylene glycol 6000 to prepare the enteric coating solution, and the solution was sprayed to give enteric coated granules. The resulting granules provided with enteric coating were found to be free from film peeling and surface roughness, being covered uniformly with enteric films.

TEST EXAMPLE 1

The enteric-coated granules as obtained in Example 4 and Reference Examples 1 and 2 were mixed with crystalline cellulose at a ratio (enteric-coated granule: crystalline cellulose) of 1:2 and 1:5, and the mixture was compressed into tablets each weighing about 200 mg and measuring 8 mm$\phi$ in outer diameter at a compression pressure of 1 ton/cm$^2$ by use of Autograph (IS-5000, manufactured by Shimadzu Seisakusho Co. of Japan), whereby magnesium stearate was used as a lubricant. The resulting tablets were placed in an auxiliary tube to be used in the disintegration test for enteric-coated granules as specified in the Japanese Pharmacopeia, 11th revised edition, then shaker in the first solution for 60 minutes in accordance with the disintegration test for enteric-coated preparations, and the contents in the enteric-coated granules having remained in the auxiliary tube were measured by means of enzymatic assay. The granules other than those covered with the enteric films according to this invention were all found to show a great decrease in the contents and to be provided with enteric films of strength inferior to the enteric film-s of this invention.

TABLE 1

| [Contents in enteric-coated granules] | | |
|---|---|---|
| Experiment section | Formulation ratio of 1:2 | Formulation ratio of 1:5 |
| Section of this invention | 90% | 98% |

TABLE 1-continued

| [Contents in enteric-coated granules] | | |
|---|---|---|
| Experiment section | Formulation ratio of 1:2 | Formulation ratio of 1:5 |
| Control section 1 | 82% | 86% |
| Control section 2 | 80% | 88% |
| Control section 3 | 65% | 66% |

TEST EXAMPLE 2

The enteric-coated granules as obtained in Reference Examples 1 and 2 were compressed into tablets by the same procedure as described in Example 2. The resultant tablets were placed in an auxiliary tube in the same manner as described in Test Example 1 and shaken in the first solution for 60 minutes in accordance with the disintegration test for enteric-coated granules. In the case of a beaker in which tablets admixed with the enteric-coated granules as obtained in Example 2 were examined, there was observed no granule falling down from the auxiliary tube containing enteric-coated granules, but tablets incorporated with other enteric-coated granules were found to have more than 15 enteric-coated granules fall down on the bottom of the beaker from the auxiliary tube. As is evident from the above, the granules being covered with the enteric films of the present invention were proven to have improved acid resistance and increased film strength.

TEST EXAMPLE 3

In the procedure of Example 4, the formulation amount of shellac alone was changed to 15 g and 385 g, while the one of polyethylene glycol 6000 alone was changed to 231 g, to prepare three different enteric coating solutions, and spraying was performed with these coating solutions to produce enteric-coated granules (Control sections 4, 5 and 6). The resultant enteric-coated granules and the enteric-coated granules (section of this invention) as obtained in Example 4 were investigated for the disintegrating property and acid resistance, and as a result, it was found that the enteric-coated granules except the ones of this invention failed to pass the disintegration and acid-resistance tests specified in the Japanese Pharmacopeia, thus being unable to be used as enteric-coated granules.

TABLE 2

| [Results of the tests of the Japanese Pharmacopeia on the enteric-coated granules] | | |
|---|---|---|
| Experiment section | Disintegrating property | Acid resistance |
| Section of this invention | o | o |
| Control section 4 | o | x |
| Control section 5 | x | o |
| Control section 6 | o | x |

TEST EXAMPLE 4

The enteric-coated granules as obtained in Example 5 and Reference Example 3 (control sections 7 and 8) were compressed into tablets by the same procedure as described in Example 2 (but with the compression pressure being raised at 2 tons/cm$^2$). The white plain tablets were all found to weigh 480 mg, measure 15 mm in major axis, 6.5 mm in minor axis and 6 mm in thickness and have a disintegration time of about 3 minutes. The resultant tablets were subjected to the disintegration test by following the same procedure as described in Test Example 1, whereupon the contents in the enteric-coated granules having remained in the auxiliary tube were measured by means of enzymatic assay. Except the granules covered with the enteric films of this invention, the granules all showed a great decrease in the content and a film strength inferior to the enteric-coated granules of this invention, as is illustrated in the following table.

TABLE 3

| [Contents in the enteric-coated granules] | |
|---|---|
| Experiment section | Content |
| Section of this invention | 85% |
| Control section 7 | 79% |
| Control section 8 | 76% |

REFERENCE EXAMPLE 4

Materials having the composition ratio described below were mixed well each other and kneaded under the addition of water.

After the kneading, the mixture was granulated by the use of extrusion granulator (Screen diameter 1.0 mmol produced by Kikusui Seisakusho Co., Ltd., Japan) and was processed to spherical granules employing a marumerizer (1,000 rpm; produced by Fuji Paudal Co., Ltd., Japan), vacuum dried at 40° C. for 16 hours, and sifted through a round sieve to obtain 12–42 mesh size of granules.

| Compound A | 600 g |
|---|---|
| Magnesium carbonate | 600 g |
| Lactose | 380 g |
| Crystalline cellulose | 160 g |
| Calcium carboxymethylcellulose | 100 g |
| Hydroxypropylcellulose | 120 g |
| Pluronic | 40 g |

EXAMPLE 6

Into a fluidized-bed coating machine (produced by Okawara Co., Japan), 1500 g of granules obtained in Reference Example 4 were charged and sprayed with the enteric coating solution described below under controlling the inlet-air temperature to 60° C. and product temperature to 45° C. to obtain enteric granules. In order to prevent static electricity, 3 g of talc and 3 g of Aerosil were added to the granules and mixed together.

| [Enteric coating solution] | |
|---|---|
| HP-55S | 310 g |
| Shellac | 62 g |
| Polyethylene glycol 6000 | 18 g |
| Talc | 36 g |
| Titanium oxide | 18 g |

REFERENCE EXAMPLE 5

Lactose granules having the compositions described below were obtained by granulating a mixed powder of lactose, corn starch and low substituted hydroxypropylcellulose making use of 10 % aqueous hydroxypropylcellulose solution in a conventional manner.

The lactose granules, enteric granules obtained in Example 6, crystalline cellulose, Ac-Di-Sol and magnesium stearate were mixed well together in the ratio described below and the mixture was tableted making use of a rotary tableting machine (produced by Kikusui Seisakusho Ltd., Japan) to obtain tablets weighing 450 mg per tablet. In the tablets each, 30 mg of Compound A is contained.

| | |
|---|---|
| Lactose granules | 1435 g |
| Lactose | 1056 g |
| Corn starch | 264 g |
| Low substituted hydroxypropylcellulose | 72 g |
| Hydroxypropylcellulose | 43 g |
| Enteric granules (obtained in Example 6) | 1300 g |
| Crystalline cellulose | 1500 g |
| Ac-Di-Sol | 250 g |
| Magnesium stearate | 15 g |

We claim:

1. An enteric film which comprises
(a) hydroxypropylmethylcellulose phthalate exhibiting a viscosity of about 136 to 204 centistokes as 10% methanol/dichloromethane (1 : 1 by weight) solution at 20° C.,
(b) polyethylene glycol presenting solid state at ambient temperature and
(c) shellac, the ratios of (b) and (c) to (a) being 0.1 to 20 weight percent and 5 to 40 weight percent, respectively.

2. An enteric film according to claim 1, wherein the contents of methoxyl, hydroxypropoxyl, and carboxybenzoyl groups in the hydroxypropylmethylcellulose phthalate are 18.0 to 22 percent, 5.0 to 9.0 percent and 27 to 35.0 percent, respectively, and the mean degree of polymerization of hydroxypropylmethylcellulose phthalate is about 240; and the polyethylene glycol presents solid state at 15 to 25° C. and has mean molecular weight of 1,200 to 25, 000.

3. An enteric film according to claim 1, wherein the polyethylene glycol is polyethylene glycol 1500, 4000, 6,000 or 20,000.

4. A process for preparing an enteric film, which comprises spraying on a material a mixed solution of (a) hydroxypropylmethylcellulose phthalate exhibiting a viscosity of about 136 to 204 centistokes as 10% methanol/dichloromethane (1 : 1 by weight) solution at 20° C., (b) polyethylene glycol presenting solid state at ambient temperature and (c) shellac, respective ratios of (b) and (c) to (a) being 0.1 to 20 weight percent and 5 to 40 weight percent; and then drying the solution.

5. A process according to claim 4, wherein the contents of methoxyl, hydroxypropoxyl and carboxybenzoyl groups in the hydroxypropylmethylcellulose phthalate are 18.0 to 22 percent, 5.0 to 9.0 percent and 27.0 to 35.0 percent, respectively, and the mean degree of polymerization of the hydroxypropylmethylcellulose phthalate is about 240; and the polyethylene glycol presents solid state at 15 to 25° C. and has mean molecular weight of 1,200 to 2,5000.

6. A process according to claim 4, wherein the polyethylene glycol is polyethylene glycol 1500, 4000, 6,000 or 20,000.

7. A process according to claim 4, wherein the material is powder, fine granules, granules, pills, tablets or capsules.

8. A process according to claim 4, wherein the solution is prepared by employing a mixture of acetone and ethanol or ethanol and water as a solvent.

9. A process according to claim 4, wherein the solution is prepared by mixing a solution of the hydroxypropylmethylcellulose phthalate in acetone and a solution of the polyethylene glycol and the shellac in ethanol.

10. A process according to claim 9, wherein the concentration of the hydroxypropylmethylcellulose phthalate in acetone is 3 to 15 weight percent, the concentration of the polyethylene glycol in ethanol is 0.1 to 5 weight percent, and the concentration of the shellac in ethanol is 1 to 10 weight percent.

11. An enteric film according to claim 2, wherein the molecular weight of the polyethylene glycol is 2,000 to 10,000.

12. An enteric film according to claim 2, wherein the molecular weight of the polyethylene glycol is 7,000 to 9,500.

13. A process according to claim 5, wherein the molecular weight of the polyethylene glycol is 2,000 to 10,000.

14. A process according to claim 5, wherein the molecular weight of the polyethylene glycol is 7,000 to 9,500.

15. A process according to claim 8, wherein the solution additionally contains isopropanol or normal propanol.

16. A process according to claim 10, wherein the concentration of hydroxypropylmethylcellulose phthalate in acetone is 6 to 10 weight percent, the concentration of polyethylene glycol in ethanol is 0.5 to 1.5 weight percent and the concentration of shellac in ethanol is 3 to 6 weight percent.

17. An enteric film comprising an admixture of:
(a) hydroxypropylmethylcellulose phthalate exhibiting a viscosity of about 136 to 204 centistokes as a 10% methanol/dichloromethane (1:1 by weight) solution at 20° C.,
(b) polyethylene glycol which is solid at ambient temperature, and
(c) shellac,
wherein the ratios of (b) and (c) to (a) are 0.1 to 20 weight percent and 5 to 40 weight percent, respectively.

* * * * *